(12) United States Patent
O'Loughlin

(10) Patent No.: US 9,101,272 B2
(45) Date of Patent: Aug. 11, 2015

(54) FIXED ANTERIOR GANTRY CT SHIELDING

(75) Inventor: Michael T. O'Loughlin, West Hartford, CT (US)

(73) Assignee: Jefferson Radiology, P.C., East Hartford, CT (US)

( * ) Notice: Subject to any disclaimer, the term of this patent is extended or adjusted under 35 U.S.C. 154(b) by 513 days.

(21) Appl. No.: 13/410,756

(22) Filed: Mar. 2, 2012

(65) Prior Publication Data

US 2012/0243657 A1  Sep. 27, 2012

Related U.S. Application Data

(60) Provisional application No. 61/465,782, filed on Mar. 24, 2011.

(51) Int. Cl.
*A61B 6/03* (2006.01)
*G21K 3/00* (2006.01)
*A61B 6/00* (2006.01)
*A61B 6/10* (2006.01)
*G21K 1/10* (2006.01)

(52) U.S. Cl.
CPC .................. *A61B 6/032* (2013.01); *A61B 6/035* (2013.01); *A61B 6/107* (2013.01); *A61B 6/4035* (2013.01); *A61B 6/4042* (2013.01); *A61B 6/4078* (2013.01); *A61B 6/482* (2013.01); *A61B 6/488* (2013.01); *A61B 6/583* (2013.01); *G21K 1/10* (2013.01)

(58) Field of Classification Search
CPC ....... G21K 1/043; G21K 1/10; A61B 6/4035; A61B 6/4042; A61B 6/482; A61B 6/032; A61B 6/035; A61B 6/107; A61B 6/488

USPC .......................... 378/5, 16, 18, 156–159, 203
See application file for complete search history.

(56) References Cited

U.S. PATENT DOCUMENTS

| 3,723,743 | A | | 3/1973 | Brackenbrough et al. |
| 5,412,562 | A | * | 5/1995 | Nambu et al. ................... 378/10 |
| 5,937,028 | A | | 8/1999 | Tybinkowski et al. |
| 6,280,084 | B1 | * | 8/2001 | Toth .............................. 378/207 |
| 6,307,918 | B1 | * | 10/2001 | Toth et al. ..................... 378/158 |

(Continued)

OTHER PUBLICATIONS

Jia Wang et al., "Radiation dose reduction to the breast in thoracic CT: Comparison of bismuth shielding, organ-based tube current modulation, and use of a globally decreased tube current," Medical Physics 38 (11), 6048 (2011).*

(Continued)

*Primary Examiner* — Allen C. Ho
(74) *Attorney, Agent, or Firm* — Alix, Yale & Ristas, LLP

(57) ABSTRACT

A radiation shield is fixed to scanning equipment at a location that attenuates a moving beam of radiation only while the beam passes over a relatively vulnerable portion, especially anterior portion, of the patient's body. Such an in-plane shield can be selective as to radiation wavelength attenuation. As an example, for scanners that use X-rays, the low energy portion of the spectrum can be selectively blocked while the high energy portion of the spectrum passes through to the patient and detector. When embodied in a CT X-ray scanner, the selective attenuation can be achieved with a thin slice bismuth shield/filter permanently installed on at least the anterior quadrant of the gantry, preferably on a span of approximately about 140 deg. in registry with the circular path of the source.

18 Claims, 5 Drawing Sheets

(56) References Cited

U.S. PATENT DOCUMENTS

| | | | |
|---|---|---|---|
| 6,501,828 B1* | 12/2002 | Popescu | 378/150 |
| 6,542,576 B2* | 4/2003 | Mattson | 378/119 |
| 6,597,758 B1* | 7/2003 | Rosner | 378/53 |
| 6,614,878 B2* | 9/2003 | Bogatu et al. | 378/158 |
| 6,633,627 B2* | 10/2003 | Horiuchi | 378/156 |
| 6,647,095 B2* | 11/2003 | Hsieh | 378/159 |
| 6,700,949 B2 | 3/2004 | Susami et al. | |
| 6,735,273 B2* | 5/2004 | Flohr et al. | 378/5 |
| 6,851,854 B2* | 2/2005 | Schmitt | 378/207 |
| 6,968,030 B2* | 11/2005 | Hoffman | 378/5 |
| 6,968,042 B2* | 11/2005 | Toth et al. | 378/156 |
| 7,076,029 B2* | 7/2006 | Toth et al. | 378/158 |
| 7,099,427 B2* | 8/2006 | Cadwalader et al. | 378/4 |
| 7,120,222 B2* | 10/2006 | Hoffman | 378/5 |
| 7,303,334 B2 | 12/2007 | Cadwalader et al. | |
| 7,330,535 B2* | 2/2008 | Arenson et al. | 378/158 |
| 7,430,282 B2* | 9/2008 | Mori et al. | 378/159 |
| 7,474,736 B2* | 1/2009 | Munro et al. | 378/159 |
| 7,510,325 B2* | 3/2009 | Endo et al. | 378/207 |
| 7,591,590 B2 | 9/2009 | Cadwalader et al. | |
| 7,826,594 B2* | 11/2010 | Zou et al. | 378/92 |
| 7,844,032 B2* | 11/2010 | Vermilyea et al. | 378/149 |
| 7,894,569 B2* | 2/2011 | Proksa | 378/5 |
| 7,905,660 B2 | 3/2011 | Sukovic et al. | |
| 7,976,218 B2* | 7/2011 | Vermilyea et al. | 378/203 |
| 8,218,728 B2* | 7/2012 | Karch | 378/98.11 |
| 8,487,287 B2* | 7/2013 | Cadwalader et al. | 250/515.1 |

OTHER PUBLICATIONS

Bradley L. Fricke et al., "In-Plane Bismuth Breast Shield for Pediatric CT: Effect on Radiation Dose and Image Quality Using Experimental and Clinical Data," American Journal of Roentgenology 180, 407 (2003).*

Mannudeep K. Kalra et al., "In-Plane Shielding for CT: Effect of Off-Centering, Automatic Exposure Control and Shield-to-Surface Distance," Korean J. Radiol. 2009; 10:156-163.*

"In-Plane Shielding for CT: Effect of Off-Centering, Automatic Exposure Control and Shield-to-Surface Distance" article by Mannudeep K. Kalra, MD, et al., Dept. of Radiology, Massachusetts General Hospital, Boston, MA 02114, USA; Korean J Radiol 10(2), Apr. 2009; pp. 156-163.

* cited by examiner

FIXED ANTERIOR GANTRY CT SHIELDING

RELATED APPLICATION

This application claims the benefit under 35 U.S.C. 119(e) of U.S. Provisional Application No. 61/465,782 filed Mar. 24, 2011 for "Fixed Anterior Gantry CT Shielding".

BACKGROUND

The present invention relates to radiation shielding in medical scanning equipment.

Computed tomography (CT) is a very useful diagnostic tool but has the disadvantage of needing X-rays (radiation) to get the desired pictures. There are several ways currently in use to reduce the radiation dose to the patient while still providing diagnostic quality images. One way is to use organ specific latex impregnated bismuth shields. These in-plane shields absorb some of the lower level X-rays that would likely be deposited in the superficial tissue immediately beneath the shields. To work effectively, the shields need to be placed on top of the patient's body before the scan is performed. Individual shields for the eyes, the thyroid, the breasts, and other organs can be used, resulting in many bismuth shields over much of the patient's anterior anatomy.

SUMMARY

According to a general aspect of the present disclosure, a radiation shield is fixed to scanning equipment at a location that attenuates a moving beam of radiation only while the beam passes over a relatively vulnerable portion, especially anterior portion, of the patient's body.

Such an in-plane shield can be selective as to radiation wavelength attenuation. As an example, for scanners that use X-rays, the low energy portion of the spectrum can be selectively blocked while the high energy portion of the spectrum passes through to the patient and detector.

When embodied in a CT X-ray scanner, the selective attenuation can be achieved with a thin slice bismuth shield/filter permanently installed on at least the anterior quadrant of the gantry, preferably on a span of approximately about 140 degrees in registry with the circular path of the source. The strip of shield remains in fixed position on the gantry, over the anterior portion of body, while the X-ray source and diametrically opposed permanent detector rotate around the patient. During each revolution of the source, the beam is attenuated while directed at the anterior of the patient but unaffected while directed at the posterior of the patient and (usually) at least some of the side of the patient.

Conventional CT scanners have a bow-tie filter in place at the X-ray source to reduce the radiation dose in the patient's peripheral tissue from the side, and other fixed filters to reduce some of the very low level X-rays, but much of the remaining low level X-rays are still deposited in the superficial tissue, never penetrating through the patient to reach the detectors on the opposite side of the patient. Such filters either revolve with the revolving source, or are uniformly distributed in fixed position on a full circle around the axis of revolution.

Adding the anterior shield according to the present disclosure, reduce the low level radiation dose even more, but only along the anterior parts of the patient. This allows the regular dose to be given along the sides and posterior parts of the patient. The required change in equipment is minimal, and the data processing remains relatively straightforward (as compared with pulsing the radiation so that the patient is exposed only while the source is at the posterior of the patient). Instead, the source beam energy spectrum remains constant throughout the rotation of the beam, but when directed at the patient's anterior the beam is dose filtered to reduce the lower energy level X-rays over the entire anterior aspect of the patient.

One of many significant advantages of the shield being permanently fixed to the equipment is that the technician need not worry about forgetting to put separate individual bismuth shields on the patient. It is a passive system, always on, and always working. An inventory of multiple shields in various sizes for various body parts can be avoided. Moreover, the technician and patient can avoid the anxiety associated with placing shields on the body of an agitated or confused patient. Another advantage is simplification and greater accuracy in the periodic calibration of the equipment.

It should be appreciated that such an angle and wavelength or dose selective shield can be implemented in other medical imaging equipment beyond X-ray CT scanners.

DETAILED DESCRIPTION

Figure 1:
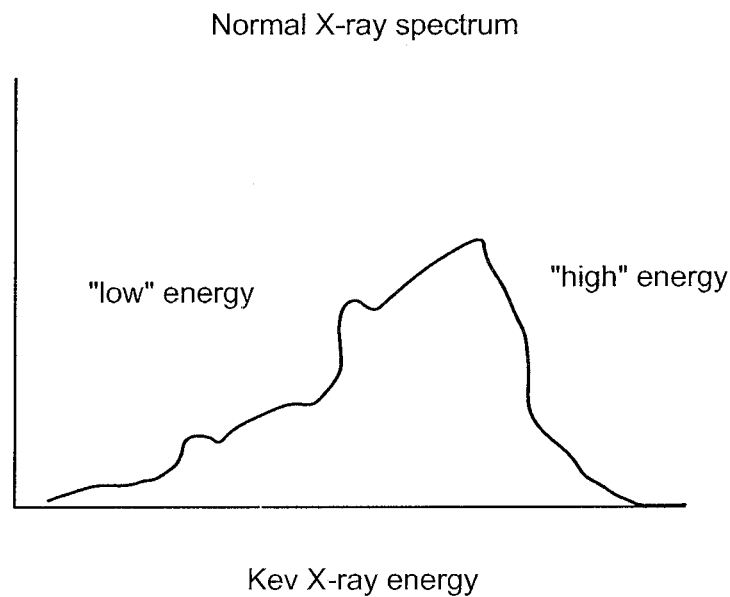
FIG. 1 is a graph representing the energy spectrum of a typical X-radiation beam used in CT scanning systems.
Figure 2:
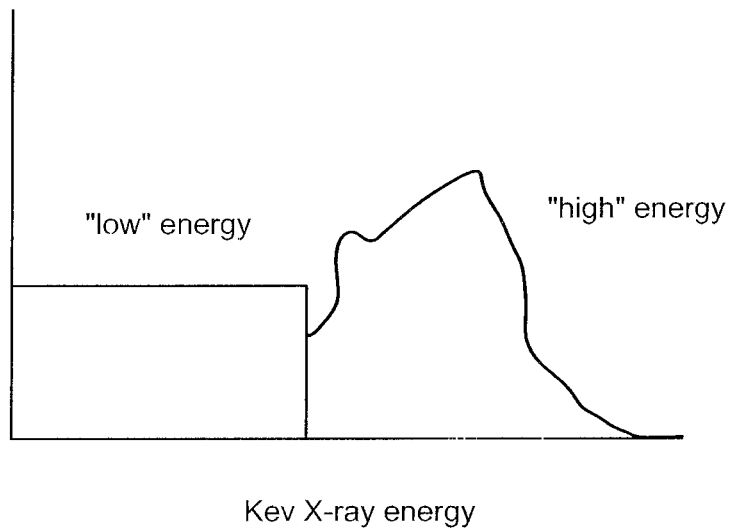
FIG. 2 is a graph similar to FIG. 1, showing how a patient shield having selective wavelength attenuation properties, can substantially reduce or eliminate the lower energy radiation of the typical beam.

FIG. 1 is a graph representing the energy spectrum of a typical X-radiation beam used in CT scanning systems and FIG. 2 is a graph similar to FIG. 1, representing how a patient shield having selective wavelength attenuation properties according to the present invention, can reduce the lower energy radiation. It is to be noted that whether or not the low energy portion of the spectrum is attenuated with a shield according to the invention, the higher energy X-rays are not as affected and can pass through the patient for the image reconstruction.

Figure 3:
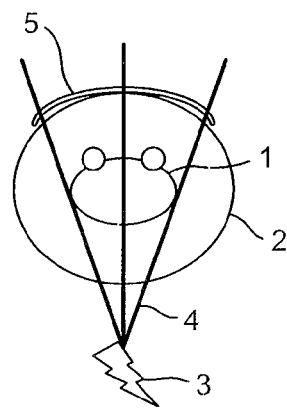
FIG. 3 is a schematic representation of an embodiment of the present invention, whereby a fixed shield above the anterior of a patient's body does not attenuate any portion of the beam passing through the anterior of the patient.
Figure 4:
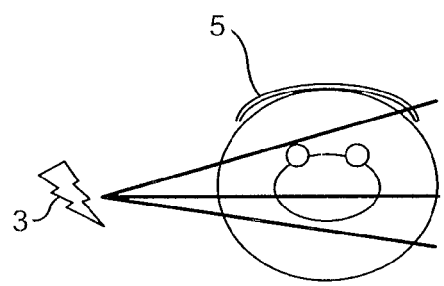
FIG. 4 is a schematic representation similar to FIG. 3, whereby the same fixed shield above the anterior of a patient's body does not attenuate any portion of the beam passing through the side of the patient.
Figure 5:
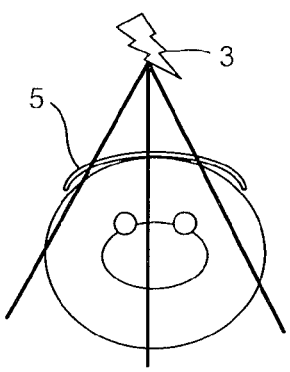
FIG. 5 is a schematic representation similar to FIG. 3, whereby the fixed shield above the anterior of a patient's body attenuates the beam that is directed toward the anterior of the patient.

The practical effect is shown in FIGS. 3-5, whereby the source angle-dependent change in the energy spectrum that reaches the patient anterior, allows the "normal" full X-ray dose to reach the sides and posterior part of the patient. Item 1 represents a patient's body lying prone with body anterior facing upward, within the main tube or stationary gantry 2 of the CT scanner. The x-ray source 3 generates an x-ray beam 4 that passes through the, patient's body 1 but the low level energy of the beam is selectively attenuated by the filter shield 5 only when the beam is directed at the anterior of the body, thereby decreasing the low level X-ray that would have deposited into the more anterior superficial tissues. This filter shield preferably spans an angle of about 140 deg. but the angle can be selected within a range of approximately 120-160 deg. according to the optimization requirements of the manufacturer or end user.

Figure 6:
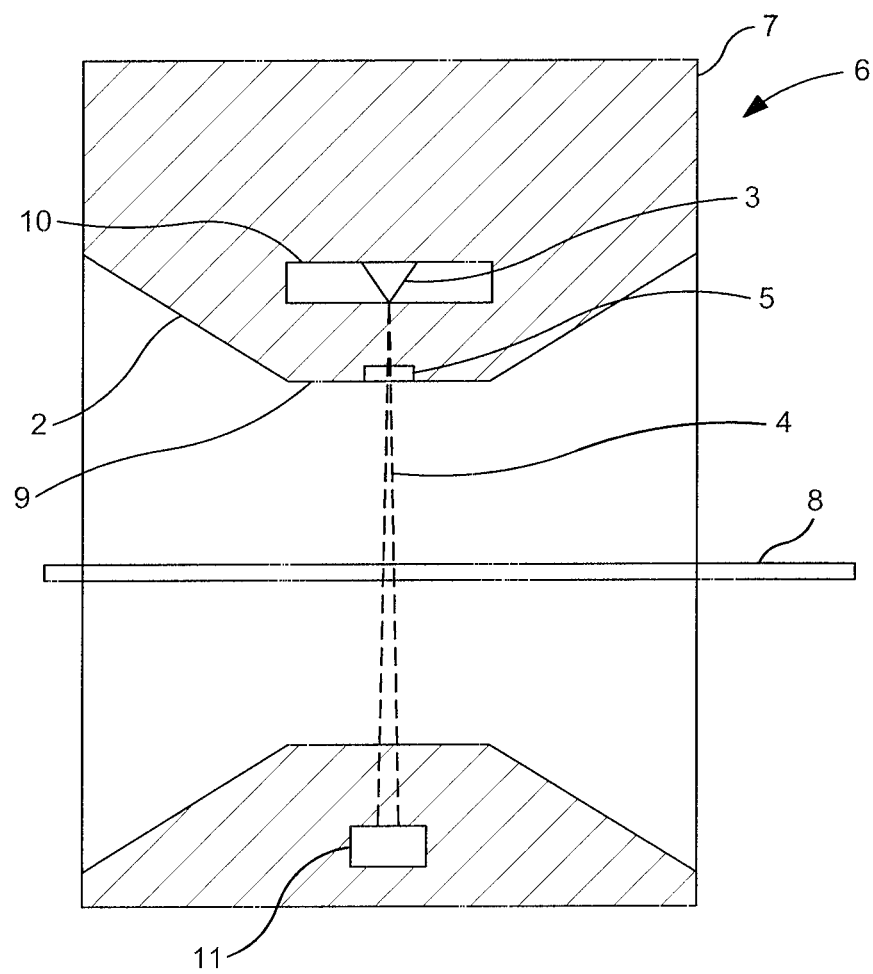
FIG. 6 is a schematic representation of a CT scanner, as seen perpendicularly to the axis of revolution of the radiation beam, with a fixed anterior shield in registry with the circular path of the beam.

A representative mounting of a thin filter shield 5 over or in front of the radiation beam channel on the interior of a tubular CT scanner is shown in FIG. 6. The overall CT scanner 6 is shown in a longitudinal cross section, and has a main frame 7 through which a patient table 8 can be inserted and removed in a tubular opening defined by a stationary gantry 2 that is somewhat bow-tie shaped as seen in this view. The middle portion 9 of the gantry is cylindrical and thereby defines a cylindrical central wall. A radiation unit 10 is situated opposite a detector unit 11, and both revolve synchronously around the longitudinal axis, aligned vertically with the cylindrical portion 9 of the gantry. The radiation unit has an x-ray source 3 that projects an x-ray beam 4 toward the detector unit 11 (and through a patient on the patient table 8). According to one embodiment of the present invention, the spectral filter shield 5 is fixed to the anterior of gantry portion 9.

The x-ray beam 4 emerges from the x-ray source 3 with a narrow depth (in the plane of the depiction shown in FIG. 6). Therefore, the width of the filter shield 5 of filter material as shown in FIG. 6 can be on the order of only a few centimeters, while the length of the strip is sufficient to span up to about 160 deg. along the inside wall of the cylindrical gantry portion 9 of the gantry (substantially in the plane depicted in FIGS. 3-5).

The filter shield 5 can be permanently mounted out of sight within the gantry (as shown), or on the inner, visible surface of the gantry, or supported by fixtures or brackets closely spaced from the surface of the gantry, so long as the advantageous functionality is achieved. An anterior gantry filter shield 5 for a CT scanner 6 would offset from the patient by at least about 15 cm, preferably in the range of approximately 20 to 30 cm depending on the size and the width of the gantry.

It can thus be appreciated from FIGS. 3-6 that the general aspect of the improvement comprises a radiation filter shield 5 mounted to the scanning device at a location that attenuates the moving x-ray beam 4 of radiation only while the x-ray beam 4 passes over a relatively vulnerable portion of the patient's body 1. In the embodiment of a CT body scanner 6, a stationary gantry 2 includes a substantially cylindrical gantry portion 9 defining a hollow cylinder into which a patient table 8 can be positioned with a patient 1 lying prone on his or her back on the patient table 8 and an anterior body portion facing the gantry portion 9. An X-ray source 3 revolves around the gantry and projects a revolving X-ray beam 4 through the gantry portion into the patient 1 on the patient table 8, whereby the x-ray beam 4 circumscribes the patient 1. A strip of radiation filter shield 5 is mounted along the gantry portion 9 of the gantry above the anterior of the patient 1 and in arcuate registry with the revolving x-ray beam 4 over a span in the range of about 120-160 deg. In this context "arcuate registry" can be understood as requiring that as the x-ray beam 4 revolves through the entire 360 deg. needed for capturing each "data slice" of the patient 1 and while the x-ray beam 4 is directed toward the anterior of the patient 1 the x-ray beam 4 must pass through the full stationary filter shield 5 along a subset arc of the revolution, preferably 120 deg.

Such a radiation filter shield can be permanently installed by the original equipment manufacturer, or customized shield units for various OEM equipment types can be manufactured by aftermarket suppliers for retro-fitting in the field.

Known bismuth impregnated latex shields are a convenient form of shielding for use in the present invention, because they are thin and flexible. However, since the filter shield 5 would be in a fixed position on the gantry, a similar benefit can be achieved with more rigid but still lightweight shields, such as an additional aluminum (or other light metal) filter shield in the gantry anterior. The metal or other material can be chosen for wavelength selectivity. Another possibility is that a suitable attenuating material can be incorporate into a tape or paint-like coating that can be adhered or applied to the gantry portion 9 of the gantry. Preferably the filter shield 5 is a curved strip that closely follows the curvature of the gantry portion 9, but the filter shield 5 can be made from a series of linear segments so long as the segments are in arcuate registry with the x-ray beam 4 as the x-ray beam 4 revolves. The angle of incidence between the x-ray beam 4 and the filter shield 5 need not be perpendicular, nor uniform.

In using equipment fitted with the filter shield 5 according to the present invention, the CT scout images which are used for localization and some automatic dose modulation techniques, should be obtained from the posterior or side position so that the auto mA would not be as affected by the anteriorly placed shields.

One of the artifacts from using flexible bismuth shields directly on a patient as in conventional techniques is the artificial increase in the Hounsfield Unit measurements below the shields. With the present invention, since the anterior filter shield 5 would always be in place, one can correct for this artifact by making accurate measurements below the anterior filter shield 5 to use for the study.

The CTDI (machine calculated specific dose measurements) would need to be adjusted to better reflect the decreased dose given to the more radiosensitive anterior structures. This would be confirmed with phantom studies/measurements when the anterior filter shield 5 is in place.

The following table contains data from tests of a type that would be used to make such corrections or otherwise calibrate the equipment when retrofitted with an embodiment of the present invention.

TABLE

| TEST # | ANTERIOR BODY SHIELD TYPE | DOSIMTER POSITION | MEASURED BODY DOSE (mSv) | MEASURED BODY DENSITY STANDARD DEVIATION (Houndsfield Units) |
|---|---|---|---|---|
| 1 | DIRECTLY ON DOSIMITER | ON BODY | 46 | 3.79/4.43 |
| 2 | DIRECTLY ON DOSIMITER | ON BODY | 48 | 3.67/4.39 |
| 3 | SLIGHTLY OFFEST FROM DOSIMITER | ON TOWEL OVER BODY | 45 | 3.65/4.41 |
| 4 | SLIGHTLY OFFEST FROM DOSIMITER | ON TOWEL OVER BODY | 46 | 3.81/4.52 |

TABLE-continued

| TEST # | ANTERIOR BODY SHIELD TYPE | DOSIMTER POSITION | MEASURED BODY DOSE (mSv) | MEASURED BODY DENSITY STANDARD DEVIATION (Houndsfield Units) |
|---|---|---|---|---|
| 5 | STRIP IN GANTRY | ON BODY 15 CM BELOW SHIELD | 41 | 4.51/4.62 |
| 6 | STRIP IN GANTRY | ON BODY SPACED 15 CM BELOW SHIELD | 43 | 4.70/4.68 |

The Table summarizes a comparison test of using one embodiment of the inventive shielding relative to two other shielding conditions. The test set up is shown schematically in FIGS. 7A-C, each of which can be considered a close-up of the layout shown in FIG. 6 with corresponding numeric identifiers. The gantry 2 has a substantially cylindrical gantry portion 9 through which the X-ray source 3 in radiation unit 10 projects a narrow x-ray beam 4 through a phantom body thorax 12a-12c on patient table 8, into the permanently mounted detector unit 11 that revolves with the x-ray source 3. The represented x-ray source 3 and detector unit 11 would revolve transversely into and out of the plane of the drawing, with one revolution producing data corresponding to one "slice" of the phantom body thorax. The body would lie longitudinally left to right along patient table 8. The represented gantry 2 or patient table 8 can be shifted incrementally to the left or right on the drawing to obtain data for many contiguous "slices" such as with x-ray beams 4' and 4" and thereby compute a "picture" of an entire region within of the body.

For the Tests reported in the Table, a substantially spherical water-filled phantom body thorax 12a-12c was placed on the patient table 8 (and as a result of gravity deformed somewhat as shown). For each Test, the geometrically fixed combination of x-ray source 3 and detector unit 11 in the gantry 2 made one revolution around the phantom body thorax and a portable detector 13a-13c on the anterior of the phantom body thorax measured the entire dose accumulated from the revolution of the X-ray source 3 on the gantry 2. The portable detector 13a-13c was a proxy for a sensitive anterior organ, such as a breast. The fourth column in the Table shows the measured body dose under the specified conditions of shield and portable detector as summarized in the second and third columns. The data in the last column are from the tomographic analysis obtained by computer processing of the output from the permanent detector unit 11 at longitudinally spaced apart positions corresponding to x-ray beams 4' and 4". The phantom body thorax 12a-12c had a length of about 195 cm and the slices taken with x-ray beams 4' and 4" were about 180 cm apart. The CT scanner 6 not only can construct a "picture" of the body internals, but can calculate densities. The two density measurements are shown on either side of the slash (/) under the specified conditions of filter shield 14a-14c and portable detector 13a-13c.

Figure 7C:
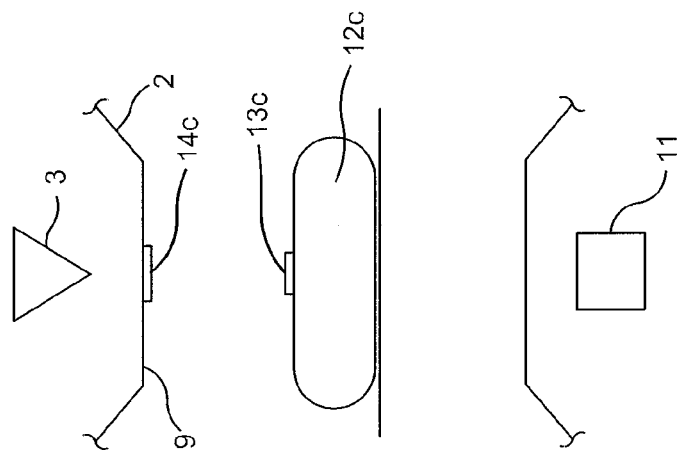
FIGS. 7 A, B, and C show three schematics representations of the conditions associated with two conventional shield configurations and an inventive configuration, respectively.
Figure 7B:
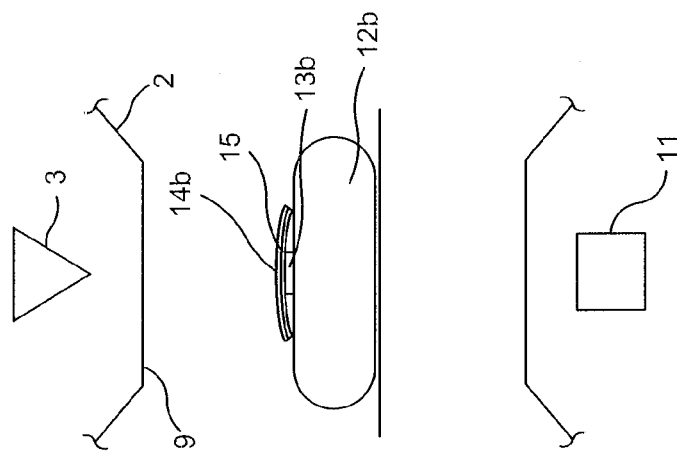
Figure 7A:
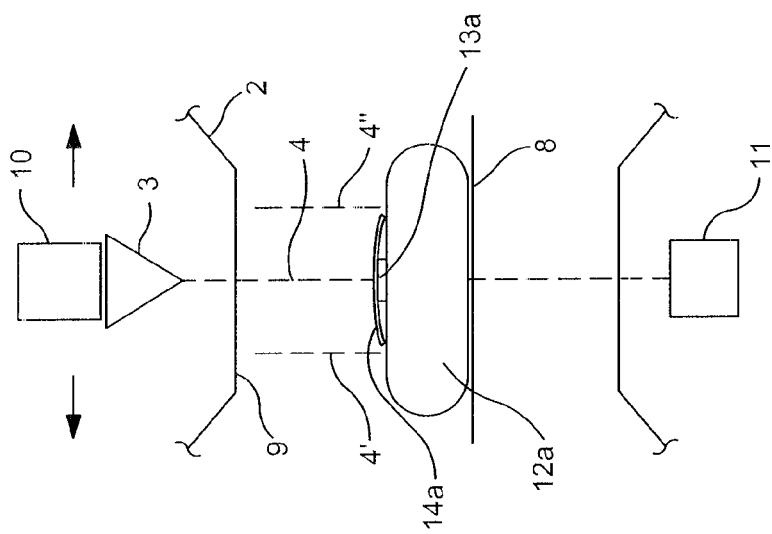

Test #'s 1 and 2 were conducted according to the representation in FIG. 7A, whereby portable detector 13a rests on the anterior of a phantom body thorax 12a and a conventionally sized (approximately 10 cm×40 cm) flexible body shield 14a of latex impregnated with bismuth lies directly on the portable detector 13a. The detector 13a, b, and c for all Tests was the same substantially flat dosimeter.

Test #'s 3 and 4 were conducted according to the representation in FIG. 7B, whereby a thick towel 15 was placed beneath the conventional flexible shield 14b and the portable detector 13b was placed on the anterior of a phantom body thorax 12b. This configuration most closely resembles typical practice in radiology, where a towel is placed on the patient over the region to be examined and the flexible shield is placed on the towel. In the corresponding tests, the portable detector 13b contacts the phantom body thorax 12b and is offset from the shield 14b by the thickness of the towel 15.

Test #'s 5 and 6 were conducted according to the representation in FIG. 7C and correspond to an embodiment of the present invention. The portable detector 13c was placed on the anterior of a phantom body thorax 12c and the shield 14c was a two-inch wide strip of latex impregnated with bismuth, attached to and spanning about 120 deg. of the cylindrical portion 9 of the gantry above the phantom body thorax 12c (i.e., into and out of the plane of the drawing). The strip shield 14c remained in fixed position over the anterior portion of a phantom body thorax 12c while the x-ray source 3 and associated permanent detector unit 11 made one revolution. At the position shown in FIG. 7C, the shield 14c was about 15 cm above the portable detector 13c.

The data reported in the Table show that with the inventive arrangement represented by FIG. 7C and Test #'s 5 and 6, the dose received by the phantom body thorax during one revolution of the x-ray source 3 is lower (average of 42 mSv) than with either conventional practice (with or without towel) represented by FIG. 7B and Test #'s 3 and 4 (45.5 mSv) and FIG. 7A and Test #'s 1 and 2 (average of 47 mSv).

The data reported in the Table also show that the inventive arrangement as tested slightly degrades the density measurement. In this context, the density of water is theoretically 0.0 on the Houndsfield unit scale. In a well-calibrated system, the phantom body thorax 12a-12c of water should likewise measure 0.0 but the actual measurements for the various tests showed one standard deviation in the range of about 3.6 to 4.7 Houndsfield units. Given that the density of air is theoretically 1000 in Houndsfield units, the measured standard deviations in the last column of the Table are within expectations given that the system was not calibrated for the tests. The more important conclusion is that the deviation of the inventive configuration (Test #'s 5 and 6) was no more than about one Houndsfield unit greater than the deviation of the two types of conventional practice (Test #'s 1-4). This means that the calculation of the picture quality will not be significantly affected by substituting the inventive technique for conventional practice, even if the equipment is not recalibrated.

However, in conventional practice the equipment must be regularly recalibrated with averaging to take into account the variety of body shields that might be used depending on the size of the patient and the organs to be protected. With the present invention, the same shield is substantially permanently fixed to the equipment and therefore calibration is simplified and more accurate. Calibration does not require sampling with a variety of shields and shield locations and then averaging the sampled data. Instead, calibration is made with the shield as already fixed to the equipment in one, invariable position, so the calibration remains accurate because all patient scans will be made with the same shield in the same invariable position.

Figure 8:
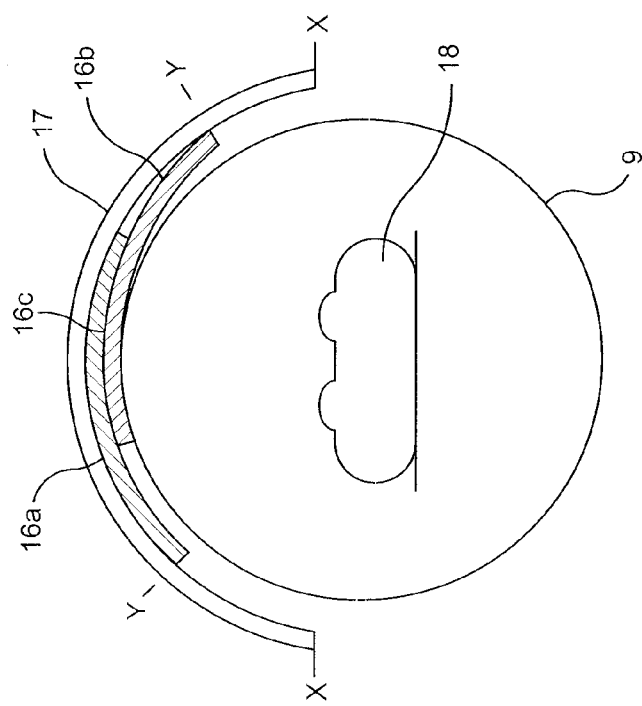
FIG. 8 shows a first alternative embodiment of the invention.

FIG. 8 shows another embodiment whereby the filter strip is segmented into portions 16a and 16b, which overlap at 16c immediately above the center of the anterior of the patient. The strip portions 16a, 16b can be on a track or channel that closely conforms to or is in the cylindrical portion 9 of the gantry and the strips can span up to about 160 deg. (between X-X). The length of each strip portion can be at least equal to ½ that span. The strip portions 16a, 16b are retained and are angularly displaceable or repositionable in the track 17 so that they can cover any selectable span between 160 deg. (X-X) and 120 deg. (Y-Y). Rather than having only two portions 16a and 16b which can overlap when shifted toward each other as at 16c when covering less than the full angular span X-X, three or four smaller segments (not shown) of, e.g., 40 degrees each could be available for end to end placement, selectively spanning 40, 80, 120 or 160 deg. above patient 18.

Figure 9:
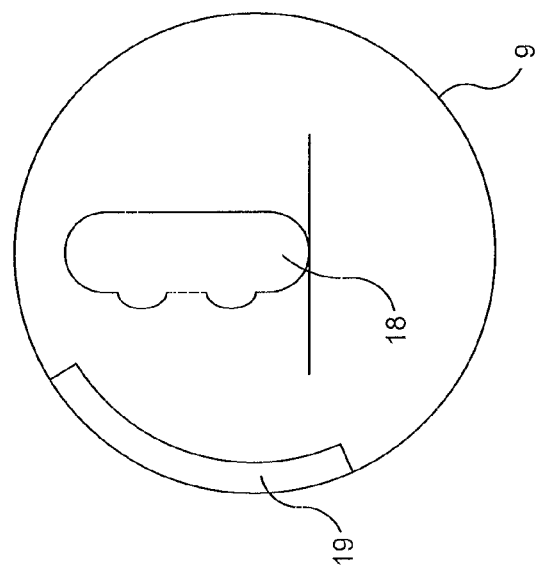
FIG. 9 shows a second alternative embodiment of the invention.

FIG. 9 shows another embodiment, employed in the occasional situation where the best diagnostic practice is to scan the patient while lying on his or her side. In this situation, the anterior of the patient 18 is facing or centered at 3:00 or 9:00 o'clock (depicted) rather than at the 12:00 o'clock orientation as depicted in FIGS. 3-8. According to the invention, the filter 19 is also centered at the 9:00 o'clock position in the cylindrical gantry portion 9, so as to span the anterior of the patient.

It should be appreciated that the embodiment shown in FIG. 8 can be adapted for use as shown in FIG. 9, by running the track 17 as a circle around the entire gantry (or at least about 270 deg. of a circle), whereby any one filter strip such as 19 or any plurality of smaller strips such as 16a and 16b can be mounted or centered anywhere on the circle to cover a span in the range of 120-160 deg.

The invention claimed is:

1. A medical radiation scanning device for imaging a region of a patient's body, comprising: a gantry defining a space for receiving said region of a patient's body; a source of a scanning beam of radiation movable around said region of a patient's body; a radiation shield fixed in the gantry in stationary relationship to the movable scanning beam at a location that attenuates the movable scanning beam of radiation only while the movable scanning beam of radiation passes over a relatively vulnerable portion of said region of the patient's body while said region of the patient's body is in said space; wherein the medical radiation scanning device is a CT body scanner that uses said scanning beam of radiation having a spectrum of X-radiation energy, and the low energy portion of the X-ray spectrum is preferentially attenuated by the radiation shield while the high energy portion passes through the radiation shield substantially unaffected.

2. The medical radiation scanning device of claim 1, wherein the gantry includes a cylindrical wall defining said space, a patient is situated in said space, the source of the movable scanning beam revolves around said region of the patient's body, and the radiation shield attenuates the spectrum only while the beam is directed to an anterior portion of said region of the patient's body.

3. The medical radiation scanning device of claim 2, including a track that conforms to the curvature of the central wall and wherein the radiation shield is mounted on said track.

4. The medical radiation scanning device of claim 3, wherein the track spans an arc of at least 270 deg. along the central wall and the strip of radiation shield is carried in the track over a span in the range of 120-160 deg.

5. The medical radiation scanning device of claim 2, wherein the radiation shield is selectively adjustable to span any angle range between 120-160 deg.

6. The medical radiation scanning device of claim 2, wherein the radiation shield is a curved strip that closely conforms to the curvature of the central wall.

7. The medical radiation scanning device of claim 6, wherein the radiation shield remains spaced from the patient by at least 15 cm.

8. A medical radiation scanning device for imaging a region of a patient's body, comprising:
a gantry including a wall defining an internal space;
a support within said space and at least said region of the patient's body supported thereon within said space;
a source of a scanning beam of radiation movable around said region of the patient's body, wherein the scanning beam contains a spectrum of radiation energy and revolves in said space around said region of the patient's body;
a radiation detector system situated with respect to the gantry wall for receiving radiation from the scanning beam, after the scanning beam has passed through said region of the patient on the support;
a radiation shield fixed in the gantry in stationary relationship to the movable scanning beam at a location that attenuates the movable scanning beam of radiation only while the beam of radiation passes over an anterior portion of said region of the patient's body while said region of the patient's body is in said space; and
wherein said detector system is sensitive to a first portion of the spectrum, and the radiation shield attenuates only a different, second portion of the spectrum only while the scanning beam is directed to an anterior portion of said region of the patient's body.

9. A medical imaging device comprising:
a gantry including a substantially cylindrical central wall defining a tubular space around a longitudinal axis;
a source of scanning radiation rotatable circumferentially a multiplicity of revolutions about the central wall, for projecting a beam of radiation transversely through the longitudinal axis throughout each revolution;
a support within the tubular space;
a radiation detector system situated with respect to the central wall for receiving radiation from the beam during each revolution of the source, after the beam has passed through a patient on the support;
a radiation shield supported at the central wall in stationary position relative to the central wall throughout each complete revolution of the rotatable source;
wherein the radiation shield extends in arcuate registry with the rotating rotatable source along only a partial circumferential span of the central wall.

10. The medical imaging device of claim 9, wherein said radiation shield is spaced from the support a sufficient distance to remain at least 15 cm offset from a patient on said support.

11. The medical imaging device of claim 9, wherein the radiation is in the X-ray energy spectrum and the radiation shield attenuates all X-rays below a threshold energy while passing sufficient higher energy X-rays to be detected by the radiation detector system.

12. The medical imaging device of claim 9, wherein the radiation shield extends in arcuate registry over a span in the range of 120-160 deg. around said axis.

13. The medical imaging device of claim 9, wherein the radiation shield contacts the central wall along said partial circumferential span.

14. A method of operating a CT medical radiation scanning device including a gantry in which a source of a beam of radiation is continuously directed toward and revolves around a patient's body, which patient's body is supported in the gantry, and in which a detector in diametric opposition to the source moves synchronously with the source to detect the beam of radiation that has passed through a circumferential slice of the patient's body, wherein the method comprises:
attenuating the beam of radiation through a radiation shield fixed to the gantry, only while the beam of radiation is directed to the anterior of the patient's body.

15. The method of claim 14, wherein
the source and detector revolve multiple revolutions for a respective multiple increments of displacement of the source and detector relative to the patient;
the radiation shield displaces incrementally in multiple corresponding increments of displacement relative to the patient;
whereby for each of said increments of the source and detector, the radiation beam passes through and is attenuated by the radiation beam shield only while the radiation beam is directed to the anterior of the patient's body.

16. The method of claim 15, wherein
the radiation beam contains a spectrum of radiation energy;
the detector is sensitive to a high energy portion of the spectrum;
the method includes attenuating a low energy portion of the spectrum with the radiation shield; and
computing an image of body internals from the detected high energy portion of the spectrum.

17. The method of claim 15, wherein the CT medical radiation scanning device is a CT body scanner that uses a radiation beam having a spectrum of X-radiation energy, and the method includes attenuating the low energy portion of the X-ray spectrum by the radiation shield while the high energy portion passes through the radiation shield substantially unaffected.

18. The method of claim 14, wherein
the radiation beam contains a spectrum of radiation energy;
the detector is sensitive to a high energy portion of the spectrum;
the method includes attenuating a low energy portion of the spectrum with the radiation shield; and
computing an image of body internals from the detected high energy portion of the spectrum.

* * * * *